United States Patent
Chen et al.

(10) Patent No.: US 8,457,916 B2
(45) Date of Patent: Jun. 4, 2013

(54) METHOD AND DEVICE FOR CALIBRATING A MAGNETIC INDUCTION TOMOGRAPHY SYSTEM

(75) Inventors: Dayu Chen, Shanghi (CN); Ming Yan, Shanghai (CN)

(73) Assignee: Koninklijke Philips Electronics N.V., Eindhoven (NL)

( * ) Notice: Subject to any disclaimer, the term of this patent is extended or adjusted under 35 U.S.C. 154(b) by 342 days.

(21) Appl. No.: 12/919,223

(22) PCT Filed: Mar. 3, 2009

(86) PCT No.: PCT/IB2009/050841
§ 371 (c)(1),
(2), (4) Date: Aug. 25, 2010

(87) PCT Pub. No.: WO2009/112965
PCT Pub. Date: Sep. 17, 2009

(65) Prior Publication Data
US 2011/0004432 A1    Jan. 6, 2011

(30) Foreign Application Priority Data
Mar. 10, 2008  (CN) .......................... 2008 1 0085233

(51) Int. Cl.
*G01D 18/00*      (2006.01)
(52) U.S. Cl.
USPC .......................................... 702/87
(58) Field of Classification Search
USPC ............................. 702/87, 95, 104
See application file for complete search history.

(56) References Cited

U.S. PATENT DOCUMENTS

| | | | |
|---|---|---|---|
| 5,872,829 A | 2/1999 | Wischmann et al. | |
| 7,146,033 B2 | 12/2006 | Brinker | |
| 7,233,145 B2 | 6/2007 | Mueller et al. | |
| 2006/0036170 A1 | 2/2006 | Lachaine et al. | |

FOREIGN PATENT DOCUMENTS

| | | |
|---|---|---|
| EP | 0479618 A2 | 4/1992 |
| WO | 2007072343 A2 | 6/2007 |

OTHER PUBLICATIONS

Rosell-Ferrer et al: "A Multifrequency Magnetic Induction Tomography System Using Planar Gradiometers: Data Collection and Calibration"; Physiological Measurement, vol. 27, 2006, pp. S271-S280.

Kappelen et al: "Drift Examination in Magnetic Induction Impedance Measurement"; Biomedizinische Technik, 48-1, 2003, pp. 328-329.

(Continued)

*Primary Examiner* — Stephen Cherry

(57) ABSTRACT

This invention relates to a method and device for calibrating the offset of an imaging system. The core idea of the invention is to place a reference object in the measurement chamber of the imaging system, measure the signals associated with the reference object at different points of time, calculate the merit function based on changes of the parameters representing the electromagnetic property of the reference object, and derive an optimal set of offset data that minimizes the value of the merit function for compensating the offset of the system in subsequent image reconstructions. In one embodiment, the invention uses a reference object comprising a non-conductive envelope and a cavity which can be filled with a conductive fluid and emptied, and in this way reduces the imaging interference caused by the reference object during monitoring.

13 Claims, 4 Drawing Sheets

OTHER PUBLICATIONS

Scharfetter et al: "Biological Tissue Characterization by Magnetic Induction Spectroscopy (MIS): Requirements and Limitations"; IEEE Transactions on Biomedical Engineering, vol. 50, No. 7, Jul. 2003, pp. 870-880.

Igney et al: "Design and Performance of a Planar-Array MIT System With Normal Sensor Alignment"; Physiological Measurement, vol. 26, 2005, pp. S263-S278.

Vauhkoven et al: "Imagereconstruction Approaches for Philips Magnetic Induction Tomograph"; ICEBI 2007, IFMBE Proceedings 17, 2007, pp. 468-471.

METHOD AND DEVICE FOR CALIBRATING A MAGNETIC INDUCTION TOMOGRAPHY SYSTEM

FIELD OF THE INVENTION

The invention relates to a method and device for calibrating an imaging system, for example, a magnetic induction tomography system.

BACKGROUND OF THE INVENTION

Magnetic induction tomography (MIT) is a non-invasive imaging technique with applications in industry and medical imaging. In contrast to other electrical imaging techniques, MIT does not require direct contact of the sensors with the object to be imaged.

MIT applies a magnetic field from one or more generator coils (also called excitation coils) to induce eddy currents in the object (i.e. material) to be studied. In other words, the scanning region is excited with a time-varying magnetic field. The presence of conductive and/or permeable material distorts the energizing field within. The perturbation of said primary magnetic field, i.e. the secondary magnetic field resulting from the eddy currents, is detected by a number of sensor coils (also called measurement coils, detection coils or receiving coils). Sets of measurements are taken and used to recover the position, shape and electromagnetic properties of the object. MIT is sensitive to all of the three passive electromagnetic properties: electrical conductivity, permittivity and magnetic permeability. As a result, for example, the conductivity contribution in a target object can be reconstructed. Because of the magnetic permeability value $\mu_R \approx 1$ of biological tissue, MIT is particularly suitable for examination of such tissue.

Prior-art patent application WO2007072343 discloses a magnetic induction tomography system for studying the electromagnetic properties of an object, the system comprising: one or more generator coils adapted to generate a primary magnetic field, said primary magnetic field inducing an eddy current in the object, one or more sensor coils adapted to sense a secondary magnetic field, said secondary magnetic field being generated as a result of said eddy current, and means for providing a relative movement between one or more generator coils and/or one or more sensor coils, on the one hand, and the object to be studied, on the other hand. By moving the generator coil or coils and/or the sensor coil or coils with respect to the target object, the number of independent measurements is increased without more coils being needed. As a result, the sensitivity matrix can be inverted more easily, the solution is more stable, and the reconstructed image has a higher spatial resolution.

The MIT system finds a major application in the field of bio-medical monitoring. The system is required to work for a long time in this case. The system offset, especially the offset caused by temperature, may affect the accuracy of the measurement. The electronic devices normally have a different phase-delay behavior in different temperature conditions, and the mechanical structure will also change when the temperature changes. All of these changes may affect the system accuracy that is required to measure within the accuracy range of milli-degrees. For this reason, the imaging system must be calibrated from time to time. In the conventional calibration method, the patient must be removed from the measurement chamber. Obviously, it is not convenient to carry out this kind of calibration when a seriously injured patient is being monitored and any movement of the patient will exacerbate his or her condition.

There is therefore a need to provide a method and device for calibrating an imaging system without movement of the monitored patient, thus improving the system accuracy.

OBJECT AND SUMMARY OF THE INVENTION

It is an object of this invention to calibrate an imaging system. The invention achieves this object by providing a method of calibrating an imaging system, the method comprising:
   a first step of measuring magnetic induction signals associated with a reference object placed in a measurement chamber of the imaging system so as to obtain a first set of measurement data;
   a step of calculating a first set of parameters based on the first set of measurement data and a set of offset data, the first set of parameters representing an electromagnetic property of the reference object, and the set of offset data being an initial estimation of the offset of the system;
   a second step of measuring magnetic induction signals associated with the reference object and an object of interest placed in the measurement chamber so as to obtain a second set of measurement data;
   a step of calculating a second set of parameters based on the second set of measurement data and the set of offset data, the second set of parameters representing the electromagnetic property of the reference object and the object of interest;
   a step of deriving a third set of parameters from the second set of parameters based on the shape and/or position of the reference object in the measurement chamber, the third set of parameters representing the electromagnetic property of the reference object; and
   a step of deriving an optimal set of offset data from the first and the third set of parameters, the optimal set of offset data being an estimation of the offset of the system; and
   a step of updating the set of offset data with the optimal set of offset data.

By calculating the merit function based on the change of the parameters representing the electromagnetic properties of the reference object and being derived from the measured signals, the method can derive an optimal set of offset data that minimizes the merit function and thus compensates the effects of the offset of the imaging system, i.e. it reduces the inaccuracy caused by the offset of the imaging system, without movement of the object of interest out of the measurement chamber.

It is advantageous that, in one embodiment, the reference object comprises a non-conductive envelope and a cavity formed by the envelope, while the method further comprises the steps of:
   filling a cavity of the reference object with a conductive fluid before the first measuring step or the second measuring step; and
   emptying the conductive fluid from the cavity after the second measuring step.

By emptying the conductive fluid from the cavity of the reference object, only the non-conductive envelope of the reference object is left in the measurement chamber, which minimizes the magnetic interferences caused by a reference object during patient monitoring and thus improves the image quality.

It is another object of this invention to calibrate the offset of an imaging system. The invention achieves this object by providing a device for calibrating the offset of an imaging system, the device comprising:

a measurement unit for measuring magnetic induction signals associated with a reference object placed in a measurement chamber of the system so as to obtain a first set of measurement data, and for measuring magnetic induction signals associated with the reference object and an object of interest placed in the measurement chamber so as to obtain a second set of measurement data;

a first calculator for calculating a first set of parameters based on the first set of measurement data and a set of offset data, and for calculating a second set of parameters based on the second set of measurement data and the set of offset data, the first set of parameters representing an electromagnetic property of the reference object, the second set of parameters representing the electromagnetic property of the reference object and the object of interest, and the set of offset data being an initial estimation of the offset of the system;

a second calculator for deriving a third set of parameters from the second set of parameters based on the known shape and/or known position of the reference object in the measurement chamber, the third set of parameters representing the electromagnetic property of the reference object;

a first processing unit for deriving an optimal set of offset data from the first and the third set of parameters, the optimal set of offset data being an estimation of the offset of the system; and a second processing unit for updating the set of offset data with the optimal set of offset data.

When the reference object comprises a non-conductive envelope and a cavity formed by the envelope, another embodiment of the device further comprises a filling unit for filling the cavity of the reference object with a conductive fluid, an emptying unit for emptying the conductive fluid from the cavity, and a first controller for controlling the filling unit and the emptying unit.

Detailed explanations and other aspects of the invention will be described below.

BRIEF DESCRIPTION OF THE DRAWINGS

The above and other objects and features of the present invention will become more apparent from the following detailed description with reference to the accompanying drawings, in which.

Identical reference numerals are used to denote similar parts throughout the Figures.

DESCRIPTION OF EMBODIMENTS

Figure 1:
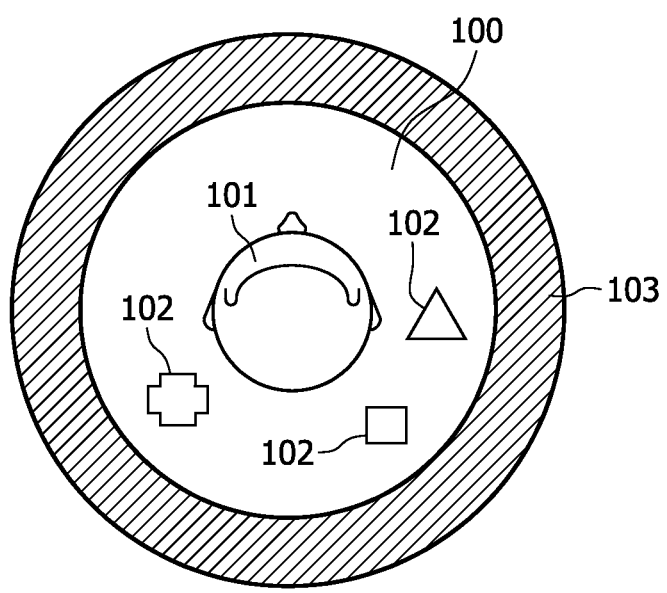
FIG. 1 is a schematic diagram showing, by way of example, an embodiment of the measurement chamber of an imaging system according to the invention.

FIG. 1 is a schematic diagram showing, by way of example, an embodiment of the measurement chamber of an imaging system according to the invention.

In the embodiment shown in FIG. 1, the measurement chamber 100, which is a part of an imaging system, is formed by a circular body 103 and is intended to accommodate objects to be imaged. The objects to be imaged define an object of interest 101 for imaging, such as the patient's head, or other parts of his body. The objects to be imaged may also include one or more reference objects 102, which may be used for calibrating the offset of the imaging system as explained hereinafter.

Figure 2:
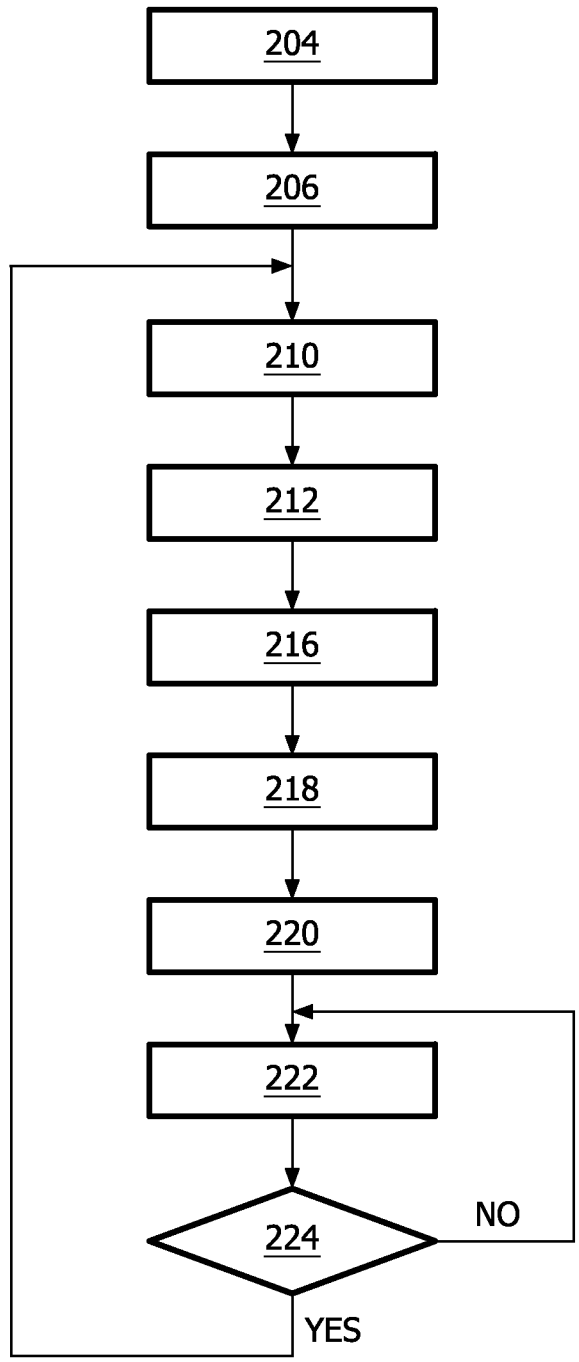
FIG. 2 is a first flowchart of the method according to the invention.

FIG. 2 is a first flowchart of a method of calibrating the offset of an imaging system.

According to the invention, the method comprises a first step 204 of measuring magnetic induction signals associated with the reference object 102 placed in the measurement chamber 100 of the system so as to obtain a first set of measurement data. The reference object 102 may comprise a couple of conductive structural objects having a predefined shape as illustrated in FIG. 1, and each structural object may be placed in a predefined position in the measurement chamber 100.

In applications of magnetic induction tomography systems for bio-medical monitoring, the first measuring step comprises the sub-steps of: generating a primary magnetic field by providing an excitation signal, the primary magnetic field inducing an eddy current in the object to be measured; and sensing a secondary magnetic field so as to generate the corresponding set of measurement data, the secondary magnetic field being generated as a result of the eddy current and represented by a set of measurement data. The first set of measurement data may comprise a phase difference vector, and each phase difference reflects a voltage difference between the excitation signal and a measured magnetic induction signal.

The method further comprises a step 206 of calculating a first set of parameters based on the first set of measurement data and a set of offset data, the first set of parameters representing an electromagnetic property of the reference object, and the initial set of offset data being an initial estimation of the offset of the system.

The calculation step 206 follows the image reconstruction theory, for example, the method of conductivity calculations and image reconstruction that are described in the prior-art document "Image reconstruction approaches for Philips magnetic induction tomograph", by M. Vauhkonen, M. Hamsch and C. H. Igney, ICEBI 2007, IFMBE Proceedings 17, pp. 468-471, 2007.

The initial set of offset data can be obtained by measuring when the measurement chamber is empty. Alternatively, the initial set of offset data can be determined by an empirical set of offset data or in combination with the measurement data for the empty measurement chamber and the empirical set of offset data.

The method further comprises a second step 210 of measuring magnetic induction signals associated with the reference object 102 and an object of interest 101 placed in the measurement chamber 100 so as to obtain a second set of measurement data. The second measuring step 210 is similar to the first measuring step 204, and the main difference is that the object to be measured includes both the reference object 102 and the object of interest 101. The object of interest 101 is placed in the measurement chamber without movement of the reference object 102 after the first measurement step 204 and has no overlap with the reference object 102 in the measurement space. The object of interest 101 may be a patient's head or some tangible material having special electromagnetic properties to be analyzed.

The method further comprises a step 212 of calculating a second set of parameters based on the second set of measurement data and the set of offset data, the second set of parameters representing the electromagnetic property of the reference object and the object of interest. Similarly as the calculation performed in step 206, the calculation step 212 follows the same image reconstruction theory, for example, by using the method described in the above-mentioned prior art.

The method further comprises a step 216 of deriving a third set of parameters from the second set of parameters based on the known shape and/or known position of the reference object in the measurement chamber, the third set of parameters representing the electromagnetic property of the reference object.

When the position of the reference object 102 in the measurement chamber 100 is known, i.e. predefined, the second set of parameters representing the electromagnetic property of the object of interest 101 and the reference object 102 can be separated into two parts: a first part, which represents the electromagnetic property of the reference object (the third set of parameters) and can be used in the following calculation of a merit function; and a second part, which represents the electromagnetic property of the object of interest (a fourth set of parameters) and can be used in the further reconstruction of an image showing a three-dimensional electromagnetic property of the object of interest.

The method further comprises a step 218 of deriving an optimal set of offset data from the first and the third set of parameters, the optimal set of offset data being an estimation of the offset of the system. In one embodiment, the deriving step 218 comprises a sub-step of calculating a merit function $F(S_1, S_3)$ defined by the following equation:

$$F(S_1, S_3) = \sqrt{\sum_{i=0}^{M-1} (\sigma_i - \sigma'_i)^2} \Big/ (M-1) \quad (1)$$

wherein $S_1$ and $S_3$ denote the first and the third set, respectively, of parameters comprising M elements, and $\sigma_i$ and $\sigma'_i$ denote the respective data values of the ith element within $S_1$ and $S_3$ i.e. the conductivity of the reference object corresponding to the ith three-dimensional point in the measurement space. The merit function is a quality indication of the third set of parameters. A smaller value of the merit function indicates a better quality of the third set of parameters. When the value of the merit function exceeds a predetermined threshold, a calibration is needed to compensate the offset of the imaging system. In such a situation, an optimal set of offset data that minimizes the value of the merit function should be found for the calibration.

The deriving step 218 further comprises a sub-step of updating the set of offset data so as to obtain an updated first and third set of parameters for calculating the merit function. The two sub-steps are performed iteratively until an optimal set of offset data that minimizes the value of the merit function is obtained.

There are many ways to derive an optimal set of offset data. For example, a Newton-Raphson optimization procedure can be used on the set of offset data so as to minimize the value of the merit function.

The method further comprises a step 220 of updating the set of offset data with the optimal set of offset data. By applying the optimal set of offset data in calculating the second set of parameters, which represents the electromagnetic property of the object to be measured, the inaccuracy caused by the offset of the imaging system can be compensated and thus self-calibrated without moving the patient out of the measurement chamber.

The method further comprises a step 222 of monitoring the object of interest. This can be done by repeatedly performing the measuring step 210, the step 212 of calculating with the updated set of offset data, a step, similar to step 216, of deriving a fourth set of parameters representing the electromagnetic property of the object of interest from an updated set of parameters representing the electromagnetic property of the object of interest and the reference object, and a step of reconstructing an image from the fourth set of parameters for the purpose of monitoring.

In another embodiment, the method further comprises a step 224 of controlling the timing to perform the calibration procedure for compensating the offset of the system. For example, the calibration procedure can be performed regularly by setting calibration intervals.

It is advantageous that the calibration procedure can be performed when it is needed. This is possible when the magnetic induction signals associated with the reference object and the object of interest are measured during continuous monitoring in step 210. In such a situation, the set of parameters obtained in step 210 can be separated into two parts as described in step 216. Then the merit function for the measurement can be calculated so as to evaluate the amount of offset of the imaging system as from its last calibration. When the value of the merit function exceeds a predetermined threshold, a calibration procedure will be performed to find the optimal set of offset data. Otherwise, the second part of the parameters, i.e. the fourth set of parameters, can be used for imaging the object of interest.

Figure 3:
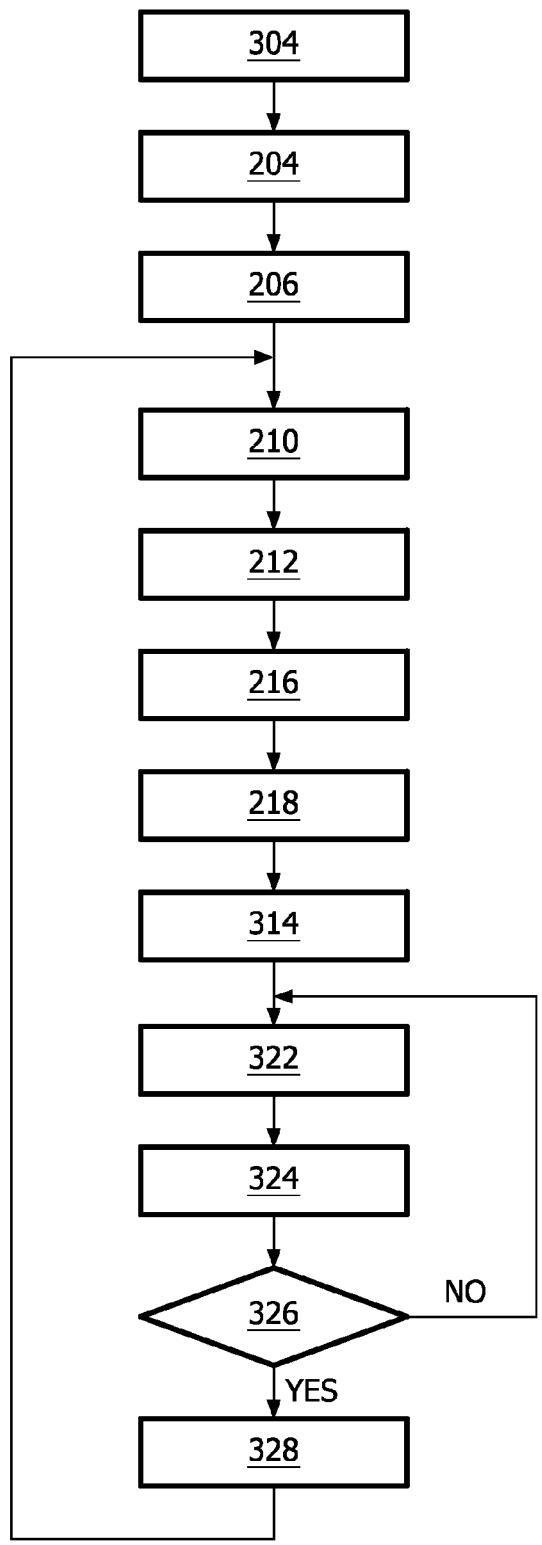
FIG. 3 is a second flowchart of the method according to the invention.

FIG. 3 is a second flowchart of a method according to the invention.

The main difference between the methods illustrated in FIGS. 2 and 3 is whether or not the signals associated with the reference object are measured when the object of interest is being monitored. In FIGS. 2 and 3, identical reference numerals are used to indicate steps having the same or a similar function.

In the calibration method referring to FIG. 3, the reference object 102 used for calibration comprises a non-conductive envelope 402 and a cavity 403 formed by the non-conductive envelope. The method further comprises a step 304 of filling a cavity 403 of the reference object 102 with a conductive fluid before the first measuring step 204, and a step 314 of emptying the conductive fluid from the cavity 403 after the second measuring step 210.

The method further comprises a step 322 of monitoring the object of interest. In this step, the object of interest can be monitored continuously by iteratively measuring signals associated with the object of interest so as to obtain a set of measurement data, calculating a set of parameters based on the set of measurement data and the set of offset data, the set of parameters representing the electromagnetic property of the object of interest, and reconstructing the image of the object of interest, using the set of parameters.

The method further comprises a step 326 of controlling the timing to perform the calibration procedure for compensating the offset of the system. When a calibration is needed, the cavity of the reference object is filled with conductive fluid again (step 328), and the procedure returns to step 210 to measure signals associated with the filled reference object and the object of interest.

In such applications, when the object of interest is being monitored during the period between two calibrations, the conductive fluid is emptied from the cavity of the reference object, and only the non-conductive envelope of the reference object is left in the measurement chamber. In this way, the imaging interference caused by a reference object, particularly the conductive fluid, is greatly reduced, which leads to a better imaging quality of the object of interest.

The above method as illustrated in FIGS. 2 and 3 can be implemented with software or hardware, both separately or in combination.

Figure 4:
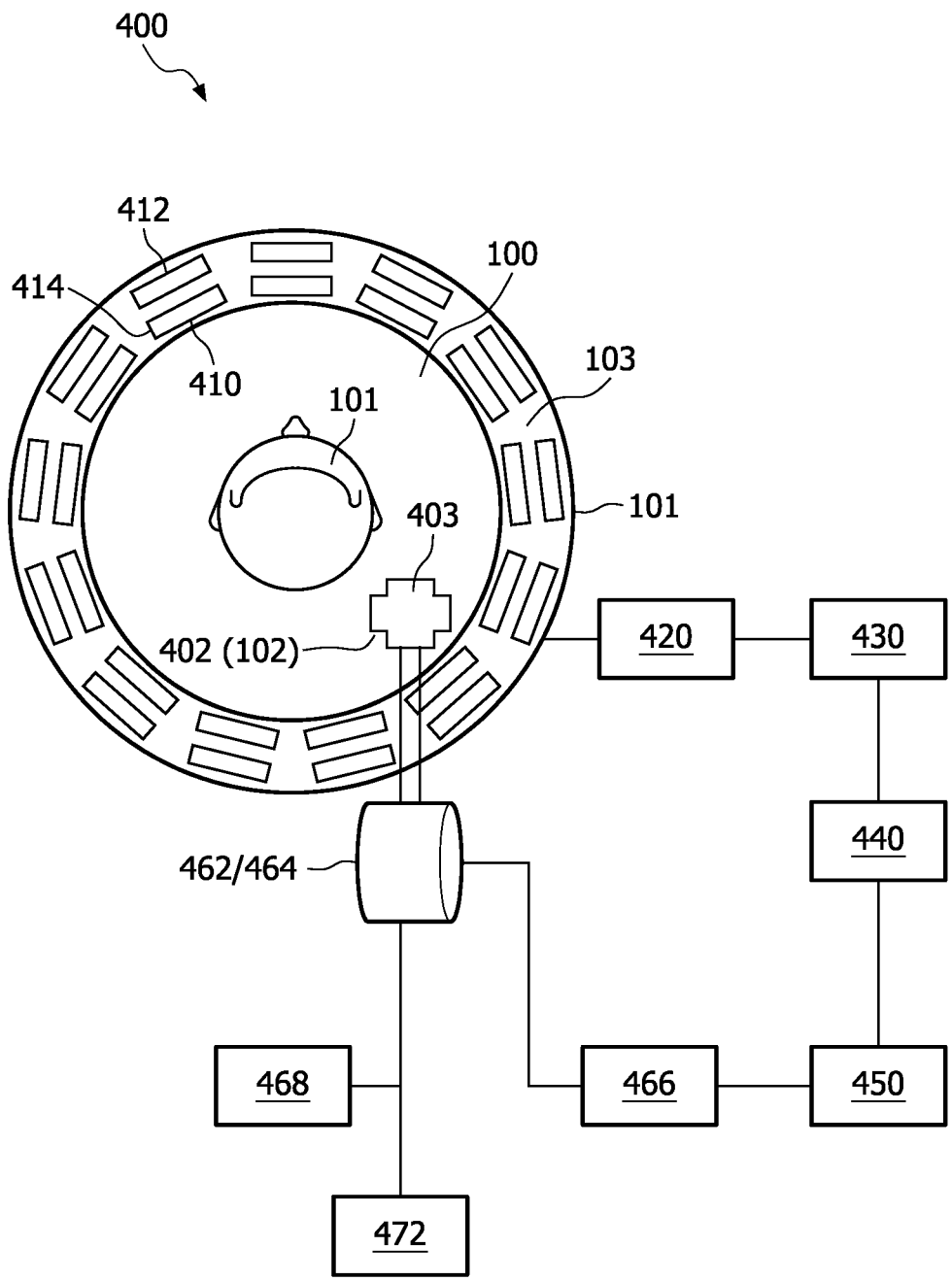
FIG. 4 is a block diagram showing, by way of example, an embodiment of the imaging system according to the invention.

FIG. 4 is a block diagram showing, by way of example, an embodiment of the calibration device 400 according to the invention.

The device 400 comprises a measurement unit 410 for measuring magnetic induction signals associated with a reference object 102 placed in a measurement chamber 100 of the system so as to obtain a first set of measurement data, and for measuring magnetic induction signals associated with the reference object 102 and an object of interest 101 placed in the measurement chamber 100 so as to obtain a second set of measurement data. The measurement unit 410 is intended to carry out the function of steps 204 and 210.

In one embodiment, the measurement unit 410 comprises one or more generator coils arranged to generate a primary magnetic field by providing an excitation signal, the primary magnetic field inducing an eddy current in the object to be measured; and one or more sensor coils arranged to sense a secondary magnetic field so as to generate the corresponding set of measurement data, the secondary magnetic field being generated as a result of the eddy current and represented by a set of measurement data.

The device 400 further comprises a measurement unit 410 for measuring magnetic induction signals associated with a reference object placed in a measurement chamber of the system so as to obtain a first set of measurement data, and for measuring signals associated with the reference object and an object of interest placed in the measurement chamber so as to obtain a second set of measurement data. The measurement unit 410 is intended to carry out the function of steps 204 and 210.

In another embodiment, the measurement unit 410 comprises one or more generator coils arranged to generate a primary magnetic field by providing an excitation signal, the primary magnetic field inducing an eddy current in the object to be measured; and one or more sensor coils arranged to sense a secondary magnetic field so as to generate the corresponding set of measurement data, the secondary magnetic field being generated as a result of the eddy current and represented by a set of measurement data.

The device further comprises a first calculator 420 for calculating a first set of parameters based on the first set of measurement data and a set of offset data, and for calculating a second set of parameters based on the second set of measurement data and the set of offset data, the first set of parameters representing an electromagnetic property of the reference object, the second set of parameters representing the electromagnetic property of the reference object and the object of interest, and the set of offset data being an initial estimation of the offset of the system. The calculator 420 is intended to carry out the function of steps 206 and 212.

The device further comprises a second calculator 430 for deriving a third set of parameters from the second set of parameters based on the known shape and/or known position of the reference object in the measurement chamber, the third set of parameters representing the electromagnetic property of the reference object. The second calculator 430 is intended to carry out the function of step 216.

The device further comprises a first processing unit 440 for deriving an optimal set of offset data from the first and the third set of parameters, the optimal set of offset data being an estimation of the offset of the system. The first processing unit 440 is intended to carry out the function of step 218.

The device further comprises a second processing unit 450 for updating the set of offset data with the optimal set of offset data, i.e. it is intended to carry out the function of step 220.

It should be noted that all or some of the first calculator 420, second calculator 430, the first processing unit 440, and the second processing unit 450 can be implemented in one processor.

It is advantageous that the reference object used for calibration comprises a non-conductive envelope 402 and a cavity 403 formed by the non-conductive envelope. In such a situation, the device 400 further comprises a filling unit 462 for filling the cavity of the reference object with a conductive fluid, and an emptying unit 464 for emptying the conductive fluid from the cavity of the reference object.

In an embodiment, the filling unit 462 and the emptying unit 464 can be implemented by a pump system which is connected to a liquid tank 468 storing conductive liquid and being controlled by a first controller 466.

The device 400 further comprises a second controller 472 for controlling the timing to measure signals associated with the reference object and the object of interest for calibrating the offset of the system, i.e. it is intended to carry out the function of steps 224 and 324.

It is advantageous that the pump system is connected to more than one liquid tank for storing different fluids having different conductivities, from different liquid tanks, while the controller can select one of these fluids in accordance with different monitoring applications.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim or in the description. Use of the indefinite article "a" or "an" preceding an element does not exclude the presence of a plurality of such elements. The invention can be implemented by means of hardware comprising several distinct elements and by means of a programmed computer. In the device claims enumerating several means, several of these means can be embodied by one and the same item of hardware or software. Use of the words first, second and third, etc. does not indicate any ordering. These words are to be interpreted as names.

The invention claimed is:

1. A method of calibrating an imaging system, the method comprising:
a first measuring step of measuring magnetic induction signals associated with a reference object placed in a measurement chamber of the imaging system, to obtain a first set of measurement data;
a step of calculating a first set of parameters based on the first set of measurement data and a set of offset data, the first set of parameter representing an electromagnetic property of the reference object and the set of offset data being an initial estimation of the offset of the system;
a second measuring step of measuring magnetic induction signals associated with the reference object and an object of interest placed in the measurement chamber (100), to obtain a second set of measurement data;
a step of calculating a second set of parameters based on the second set of measurement data and the set of offset data, the second set of parameters representing the electromagnetic property of the reference object and the object of interest;
a step of deriving a third set of parameters from the second set of parameters based on the shape and/or position of the reference object in the measurement chamber, the third set of parameters representing the electromagnetic property of the reference object; and
a step of deriving an optimal set of offset data from the first and third set of parameters, the optimal set of offset data being an estimation of the offset of the system; and
a step of updating the set of offset data with the optimal set of offset data.

2. The method as claimed in claim 1, further comprising the steps of:
filling-in a conductive fluid into a cavity of the reference object before the first measuring step or the second measuring step; and
emptying the conductive fluid from the cavity after the second measuring step.

3. The method as claimed in claim 1 further comprising a step of controlling the timing to measure signals associated with the reference object and the object of interest for calibrating the offset of the system.

4. The method as claimed in claim 3 wherein the steps of measuring comprising the steps of:
generating a primary magnetic field by providing an excitation signal, the primary magnetic field inducing an eddy current in the object to be measured; and
sensing a secondary magnetic field to generate the corresponding set of measurement data, the secondary magnetic field being generated as a result of the eddy current and represented by a set of measurement data.

5. The method as claimed in claim 4, wherein the step of deriving an optimal set of offset data comprises iterative sub-steps of
calculating a merit function according to the following equation:

$$F(S_1, S_3) = \sqrt{\sum_{i=0}^{M-1} (\sigma_i - \sigma'_i)^2 \Big/ (M-1)}$$

wherein $S_1$ and $S_3$ respectively denotes the first and third sets of parameters comprising M elements, $\sigma_i$ and $\sigma'_i$ respectively denotes the data value of the ith element $S_1$ and $S_3$, and $F(S_1,S_3)$ denotes the merit function; and
updating the set of offset data to obtain an updated first set and third set of parameters for calculating the merit function until an optimal set of offset data that minimizes the value of the merit function is obtained.

6. The method as claimed in claim 5, wherein each data in each set of measurement data corresponds to a phase difference responsive to the excitation signal, and each data in each set of parameters corresponds to a conductivity estimation of the object to be measured at a position in the measurement chamber.

7. The method as claimed in claim 6, wherein an initial estimation of the set of offset data is determined by measuring magnetic induction signals associated with the measurement chamber that is empty and/or by a predefined set of offset data.

8. A device for compensating an offset of an imaging system, comprising:
a measurement unit for measuring magnetic induction signals associated with a reference object placed in a measurement chamber of the system to obtain a first set of measurement data, and measuring magnetic induction signals associated with the reference object and an object of interest placed in the measurement chamber to obtain a second set of measurement data;
a first calculator for calculating a first set of parameters based on the first set of measurement data and a set of offset data and for calculating a second set of parameters based on the second set of measurement data and the set of offset data, the first set of parameter representing an electromagnetic property of the reference object, the second set of parameters representing the electromagnetic property of the reference object and the object of interest, and the set of offset data being an initial estimation of the offset of the system;
a second calculator for deriving a third set of parameters from the second set of parameters based on the known shape and/or known position of the reference object in the measurement chamber, the third set of parameters representing the electromagnetic property of the reference object;
a first processing unit for deriving an optimal set of offset data from the first and third set of parameters, the optimal set of offset data being an estimation of the offset of the system; and
a second processing unit for updating the set of offset data with the optimal set of offset data.

9. The device as claimed in claim 8, wherein the reference object comprises a non-conductive envelop and a cavity formed by the envelop, the device further comprises a filling-in unit for filling-in a conductive fluid into the cavity of the reference object, an emptying unit for emptying the conductive fluid from the cavity and a first controller for controlling the filling-in unit and the emptying unit.

10. The device as claimed in claim 9, wherein the filling-in unit and the emptying unit are implemented by a pump system, which is connected to at least one liquid tank storing liquid.

11. The device as claimed in claim 8, further comprising a second controller for controlling the timing to measure signals associated with the reference object and the object of interest for calibrating the offset of the system.

12. The device as claimed in claim 11, wherein the measurement means comprises:
one or more generator coils arranged for generating a primary magnetic field by providing an excitation signal, the primary magnetic field inducing an eddy current in the object to be measured; and
one or more sensor coils arranged for sensing a secondary magnetic field to generate the corresponding set of measurement data, the secondary magnetic field being generated as a result of the eddy current and represented by a set of measurement data.

13. An imaging system comprising a device as claimed in claim 8.

* * * * *